(12) United States Patent
Filice

(10) Patent No.: US 11,006,865 B2
(45) Date of Patent: May 18, 2021

(54) DETERMINING VIABILITY FOR RESUSCITATION

(71) Applicant: Anthony Filice, Ancaster (CA)

(72) Inventor: Anthony Filice, Ancaster (CA)

( * ) Notice: Subject to any disclaimer, the term of this patent is extended or adjusted under 35 U.S.C. 154(b) by 1077 days.

(21) Appl. No.: 15/372,375

(22) Filed: Dec. 7, 2016

(65) Prior Publication Data

US 2017/0160262 A1    Jun. 8, 2017

Related U.S. Application Data (60) Provisional application No. 62/264,831, filed on Dec. 8, 2015.

(51) Int. Cl.
| | |
|---|---|
| *A61B 5/15* | (2006.01) |
| *A61B 5/00* | (2006.01) |
| *G01N 33/50* | (2006.01) |
| *G01N 33/84* | (2006.01) |

(52) U.S. Cl.
CPC ........... *A61B 5/1411* (2013.01); *A61B 5/00* (2013.01); *G01N 33/50* (2013.01); *G01N 33/84* (2013.01); *G01N 2800/00* (2013.01)

(58) Field of Classification Search
CPC .... G01N 33/49; G01N 33/50; G01N 2800/60; A61B 5/02; A61B 5/14; A61B 5/00; A61B 5/15; A61B 5/1411
See application file for complete search history.

(56) References Cited

U.S. PATENT DOCUMENTS

| | | |
|---|---|---|
| 4,819,752 A | 4/1989 | Zelin |
| 5,149,503 A | 9/1992 | Kohno et al. |
| 5,490,523 A | 2/1996 | Isaacson et al. |
| | (Continued) | |

FOREIGN PATENT DOCUMENTS

| | | |
|---|---|---|
| CA | 2074029 | 1/1993 |
| CN | 201431459 | 3/2010 |
| | (Continued) | |

OTHER PUBLICATIONS

Bossaert et al., "European Resuscitation Council Guidelines for Resuscitation 2015 Section 11. The ethics of resuscitation and end-of-life decisions," European Resuscitation Council, Resuscitation 95 (2015) pp. 302-311, Elsevier Ireland Ltd.

*Primary Examiner* — Catherine M Voorhees
(74) *Attorney, Agent, or Firm* — Steven M. Greenberg, Esq.; Shutts & Bowen LLP (57) ABSTRACT

Portable automated systems and methods can be used to perform field testing of patient blood chemistry to determine whether biological death has occurred in a clinically dead patient, and therefore whether the patient is a viable candidate for resuscitation efforts. A blood sample is received in a detector, which analyzes the blood sample to generate a signal representing at least one blood chemistry parameter of the blood sample and transmits a signal representing the at least one blood chemistry parameter to a processor. The processor compares the at least one blood chemistry parameter to a corresponding at least one resuscitatability parameter and, based on the comparison, causes an indicator to emit a resuscitatability indicator signal indicating potential resuscitatability, such as "resuscitatable", "non-resuscitatable" or "borderline"/"indeterminate".

7 Claims, 4 Drawing Sheets

(56) References Cited

U.S. PATENT DOCUMENTS

| | | |
|---|---|---|
| 6,330,468 B1 | 12/2001 | Scharf |
| 6,498,652 B1 | 12/2002 | Varshneya et al. |
| 6,731,962 B1 | 5/2004 | Katarow et al. |
| 2002/0173725 A1* | 11/2002 | Rock ............... A61B 5/061 600/500 |
| 2007/0024946 A1* | 2/2007 | Panasyuk ........ A61B 5/0059 359/253 |
| 2007/0100213 A1* | 5/2007 | Dossas ............ A61B 5/1112 600/300 |
| 2008/0208009 A1 | 8/2008 | Shklarski |
| 2012/0215075 A1* | 8/2012 | Surace ............ A61B 5/0002 600/301 |
| 2014/0329214 A1 | 11/2014 | Bitoun |
| 2014/0357963 A1 | 12/2014 | Chang et al. |
| 2019/0072570 A1* | 3/2019 | Chapman ........... G01N 11/00 |

FOREIGN PATENT DOCUMENTS

| | | |
|---|---|---|
| CN | 201510286 | 6/2010 |
| CN | 201912070 | 8/2011 |
| CN | 201929960 | 8/2011 |
| CN | 202128471 | 2/2012 |
| CN | 202223225 U | 5/2012 |
| CN | 202235382 U | 5/2012 |
| CN | 202619660 U | 12/2012 |
| CN | 202776284 U | 3/2013 |
| CN | 103251393 | 8/2013 |
| CN | 203280393 U | 11/2013 |
| CN | 203539355 U | 4/2014 |
| CN | 203576483 U | 5/2014 |
| CN | 104207788 | 12/2014 |
| DE | 4313524 | 1/1994 |
| JP | 05228131 | 9/1993 |
| JP | 09122105 | 5/1997 |
| JP | 2004258761 | 9/2004 |
| JP | 2004351107 | 12/2004 |
| JP | 2011030990 | 2/2011 |
| WO | 2014106873 | 7/2014 |

* cited by examiner

DETERMINING VIABILITY FOR RESUSCITATION

CROSS-REFERENCE TO RELATED APPLICATION

This application claims priority to U.S. Provisional Application No. 62/264,831 filed on Dec. 8, 2015, the teachings of which are hereby incorporated by reference.

TECHNICAL FIELD

The present disclosure relates to paramedic response, and more particularly to determining when resuscitation efforts are warranted.

BACKGROUND

"There's a big difference between mostly dead and all dead." Those were the words of the character Miracle Max (played by Billy Crystal) in the classic film "The Princess Bride". Although the film is set in a fictional medieval world, Miracle Max's words carry an important truth in the age of modern medicine. Modern practitioners speak of patients being either clinically dead, or biologically dead. The term "clinical death" refers to a case where a patient has stopped breathing and has no heartbeat, whereas "biological death" is the point at which the tissues and organs die from lack of blood and oxygen. An individual who has suffered clinical death but not biological death ("mostly dead") can potentially be resuscitated, whereas an individual who is biologically dead ("all dead") cannot be resuscitated because the relevant aspects of the patient's biochemistry have deteriorated too far. More particularly, biological death typically occurs some time after clinical death, and it is often possible, by application of appropriate emergency treatment such as CPR and defibrillation, to prevent a clinically dead individual from deteriorating to the point of biological death. This may enable the cause(s) of clinical death to be treated so that the patient can eventually be revived. The application of medical treatment designed to prevent the onset of biological death in a clinically dead individual is referred to herein as "resuscitation".

SUMMARY

Portable automated systems and methods can be used to perform field testing of patient blood chemistry to determine whether biological death has occurred in a clinically dead patient, and therefore whether the patient is a viable candidate for resuscitation efforts.

BRIEF DESCRIPTION OF THE DRAWINGS

These and other features will become more apparent from the following description in which reference is made to the appended drawings wherein.

DETAILED DESCRIPTION

Although in some cases it may be obvious that biological death has occurred, such as where there is visible decomposition, in many cases it is difficult even for highly trained paramedics to distinguish between clinical death and biological death in the field. The result is that paramedics may squander their efforts on patients who simply cannot be revived.

This is not merely a matter of futile effort—in a world of limited resources, time spent by paramedics on a biologically dead individual may result in paramedics arriving too late to save another individual. In addition, costly drugs and supplies may be wasted. Perhaps most importantly, since every "lights and siren" transport carries inherent risk, transporting a biologically dead patient to the hospital on an emergency basis endangers the lives of paramedics and the public for no good reason.

Paramedics and ambulances are a scarce resource. If there are more emergencies than nearby ambulances, paramedics may be wasting time trying to revive a biologically dead victim even while a clinically dead patient who could be saved deteriorates beyond the point of resuscitation and also dies.

Certain markers can distinguish between a patient who is biologically dead and a patient who is only clinically dead but not biologically dead. Certain particularly useful markers are found in the blood—if a patient's blood cannot perform its biologically required functions, this loss of biological function indicates that the patient is biologically dead and hence non-resuscitatable. Thus, when blood oxygenation falls below a certain point, $CO_2$ concentration/blood acidity rises above a certain point and a sufficient amount of blood haemoglobin denatures, the patient will be biologically dead. Although portable blood testing equipment exists, it is used for general diagnostic and treatment applications and is designed to test for a wide range of blood markers, making it quite expensive and typically used only for specialized applications such as secondary and tertiary hospitals and air ambulances (e.g. helicopters). This equipment is presently manufactured by Abbott Point of Care Inc., Alere, Roche and Siemens for example.

The present disclosure contemplates an automated method for using blood chemistry to determine resuscitatability and apparatus for implementing the method. Such apparatus may be purpose-built, or may be adapted from existing blood testing equipment. The automated method is intended primarily for application by paramedics "in the field", and as such suitable apparatus will preferably be portable. For example, it is contemplated that the portable handheld blood testing devices offered by Abbott Point of Care Inc., having an address at 400 College Road East, Princeton, N.J. 08540, U.S.A., under the trademark "i-STAT"®, or by Alere Inc., having an address at 51 Sawyer Road, Suite 200, Waltham, Mass. 02453-3448, U.S.A. under the trademark "epoc"®, may be adapted for use as apparatus for implementing the presently described method.

Figure 1:
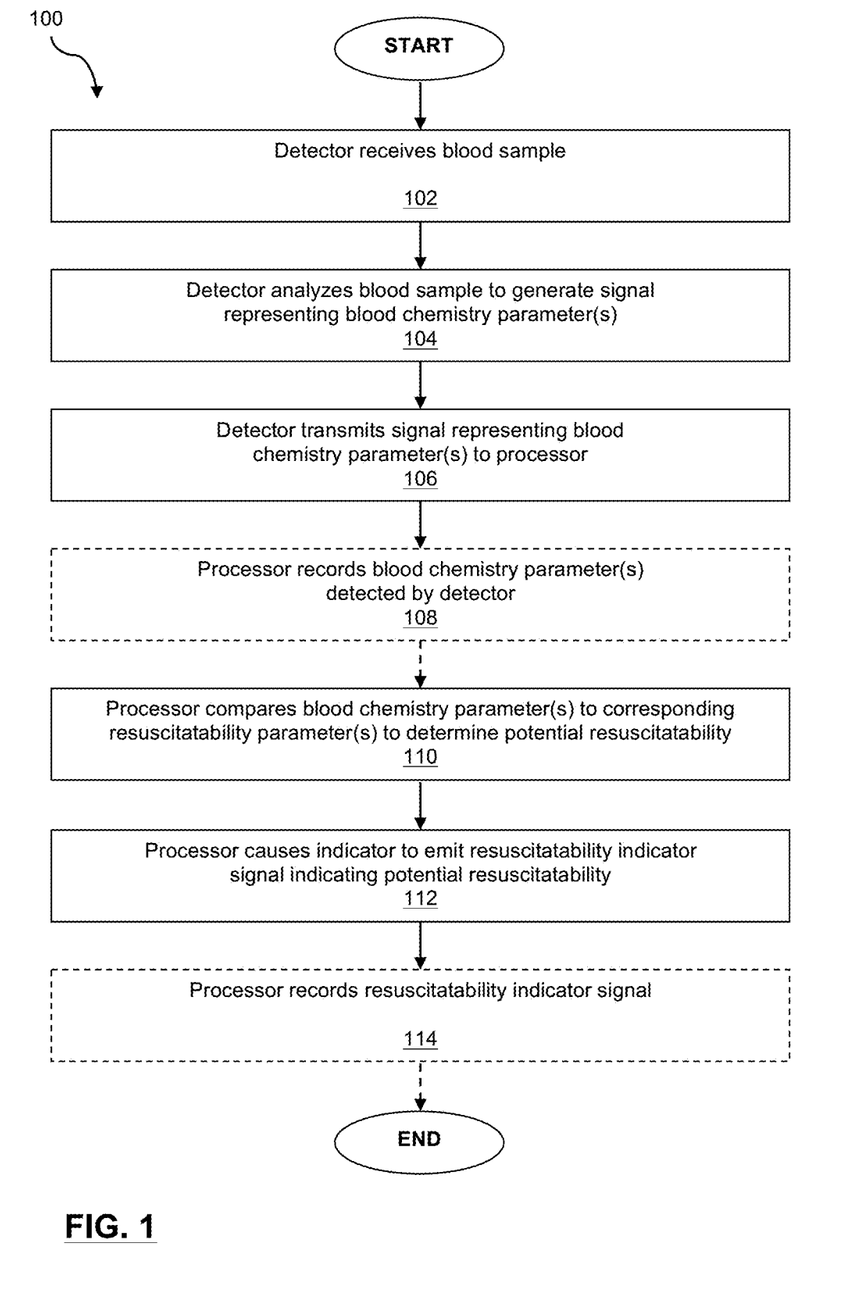
FIG. 1 is a flow chart showing an exemplary method for using blood chemistry to determine resuscitatability of a human individual.

Reference is now made to FIG. 1, which is a flow chart showing an exemplary method 100 for using blood chemistry to determine resuscitatability of a human individual. At step 102, a blood sample is received in a detector. At step 104, the detector analyzes the blood sample to generate a signal representing at least one blood chemistry parameter of the blood sample as detected by the detector, and at step 106 the detector transmits the signal representing the blood chemistry parameter(s) to a processor. The blood chemistry parameter(s) may include or be based upon, for example, one or more of pH level, lactate/lactic acid level, pyruvate level, glucose level, levels of certain fats, levels of certain clotting factors, carbonic anhydrase level, bicarbonate level, $O_2$ saturation level and possibly ATP level. The detector and the processor may be integrated, for example the detector may communicate with the processor to perform analysis of the blood sample at step 104. At optional step 108, shown in dashed lines, the processor records the blood chemistry parameter(s) detected by the detector.

At step 110, the processor compares the blood chemistry parameter(s) to a corresponding at least one resuscitatability parameter to determine whether the patient is resuscitatable. Preferably, the comparison is done such that Type II errors (falsely determining that a biologically dead patient is not biologically dead and hence resuscitatable) are the dominant error mode, rather than Type I errors (failing to detect biological death in a patient who is in fact biologically dead). The comparison at step 110 may be performed in a number of ways. In the simplest embodiment, the signal generated from the analysis at step 104 represents a single blood chemistry parameter, and at step 110 this single blood chemistry parameter is compared to a single resuscitatability parameter. For example, the single blood chemistry parameter may be the pH level of the blood. In this example, if at step 104 the detector analyzes the blood sample to generate a signal representing the pH level of the blood sample, then at step 110 the resuscitatability parameter may be a range (i.e. defining upper and lower limits) of blood pH for a person who, even if clinically dead, is not biologically dead (i.e. a clinically dead person whose blood pH is above or below the range is known to be not only clinically dead but also biologically dead and therefore not resuscitatable). Normal blood pH is between 7.36 and 7.44 and a blood pH outside of the 7.00 to 7.70 range is considered to be incompatible with life (*Survival from profound metabolic acidosis due to hypovolaemic shock. A world record*? Di Rollo N, et al. BMJ Case Rep 2013). Acidosis resulting in death is likely to occur below a pH of 6.8 while alkalosis resulting in death is likely to occur above a pH of 7.8, although blood pH typically has to remain at those extreme levels for a significant period for death to ensue, and the resuscitatability parameter for pH may be set at a range from 6.0 to 9.0, with a blood pH within that range being characterized as resuscitatable. While this range would likely categorize some individuals who are in fact biologically dead as resuscitatable (a Type II error), it is preferable to do this than to incorrectly categorize a patient who is not biologically dead as non-resuscitatable (a Type I error). This is merely one example of a pH range that may be used as a resuscitatability parameter; other suitable pH ranges may also be used. Similarly, the lactate/lactic acid level in the blood may also be used as a single blood chemistry parameter. In such an embodiment, at step 104 the detector may analyze the blood sample to generate a signal representing the lactate/lactic acid level in the blood, and at step 110 the resuscitatability parameter may be an upper bound selected to provide the desired balance between the risk of Type I error and Type II error.

In more complex embodiments, multiple blood chemistry parameters may be compared to multiple resuscitatability parameters. In some embodiments, the comparison can be done on a one-to-one basis, with each blood chemistry parameter being compared to a single corresponding resuscitatability parameter (e.g. blood pH can be compared to a predetermined range and blood lactate/lactic acid level can be compared to a predetermined upper bound), after which the processor can execute suitable logic to determine, based on the comparison, whether the patient is resuscitatable. In other embodiments, various blood chemistry parameters may be used as inputs to a formula, and the resulting value can be compared to a resuscitatability parameter (e.g. a value or a range) to determine, based on the comparison, whether the patient is resuscitatable.

Responsive to the comparison at step 110, at step 112 the processor causes an indicator to emit a human-comprehensible resuscitatability indicator signal indicating potential resuscitatability. Importantly, the resuscitatability indicator signal is not merely an indication of the value of the at least one blood chemistry parameter which is subject to medical interpretation, but provides discrete indications of whether or not the patient is biologically dead, and therefore of whether or not the patient is resuscitatable. For example, the resuscitatability indicator signal may be a binary signal indicating one of "resuscitatable" and "non-resuscitatable", or may be a trinary signal indicating one of "resuscitatable", "non-resuscitatable" and "borderline" or "indeterminate". Each of these indications is discrete. The resuscitatability indicator signal may be a visual signal, an audio signal, a combination of an audio signal and a visual signal, a printout, or any other suitable signal. In some embodiments where blood chemistry parameters are used as inputs to a formula, the resulting value can be used as a resuscitatability indicator signal which provides discrete indications of whether or not the patient is biologically dead by reference to predetermined cut-off values. For example, and without limitation, a formula may produce a value between 0 and 10, with values below 5.0 corresponding to "non-resuscitatable" and, value of 5.0 and above corresponding to "resuscitatable", below 5.0 corresponding to "non-resuscitatable", values above 7.0 corresponding to "resuscitatable", and values between (and including) 4.0 and 7.0 corresponding to "borderline" or "indeterminate".

The resuscitatability indicator signal can be used by paramedics, firefighters, police officers or other emergency personnel to obtain a rapid assessment of whether continued resuscitation efforts are warranted. For example, upon arriving at an incident scene where a victim is clinically dead, paramedics could initiate resuscitation procedures and also apply the method 100. If the resuscitatability indicator signal indicates that the patient is "resuscitatable" (or "borderline"/"indeterminate" in the case of a trinary signal) the paramedics would continue their efforts, whereas if the resuscitatability indicator signal indicates that the patient is "non-resuscitatable" the paramedics would cease treatment. The method 100 may also be applied in triage situations where prioritization of treatment is important.

At optional step 114, shown in dashed lines, the processor records the resuscitatability indicator signal. Recording the at least one blood chemistry parameter at step 108 and/or recording the resuscitatability indicator signal at step 114 can, either alone or in conjunction with other steps, provide for audit functionality. For example, suppose a paramedic were to discontinue treatment on the basis of the resuscitatability indicator signal and the patient is later ruled to be legally dead. A family member of the deceased patient could commence litigation against the paramedic (and/or his or her employer) alleging that had the paramedic continued treatment, the patient would have survived. The recorded blood chemistry parameter (step 108) could provide evidence to support expert testimony from a physician that the patient was in fact biologically dead at the time treatment was discontinued, showing an absence of causation. Similarly, the recorded resuscitatability indicator signal (step 114) can provide evidence that the paramedic acted reasonably in discontinuing treatment based on the available information. To facilitate the evidentiary value of the recorded blood chemistry parameter (step 108) and recorded resuscitatability indicator signal (step 114), they may be recorded in association with timestamp and location data (e.g. the processor may be coupled to a GPS unit or other location processor).

Figure 2:
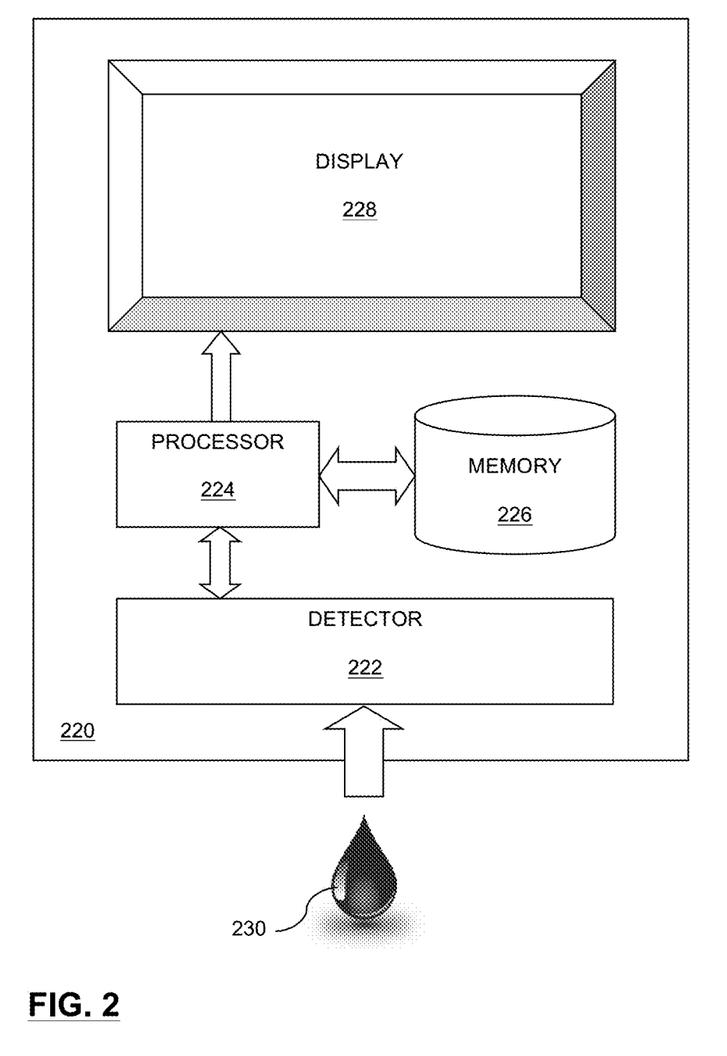
FIG. 2 is a simplified schematic illustration of an exemplary apparatus for using blood chemistry to determine resuscitatability of a human individual.

Reference is now made to FIG. 2, in which an exemplary testing apparatus 220 for using blood chemistry to determine resuscitatability, for example according to the method 100 shown in FIG. 1, is shown. The apparatus 220 is shown in simplified schematic form in which certain key components are shown with other components being omitted for simplicity of illustration. The apparatus is portable, so that it can conveniently fit inside an ambulance, and is preferably small enough and light enough to be easily carried by a paramedic, police officer, firefighter or other first responder. The apparatus 220 may be purpose-built or may be, for example, a suitably modified i-STAT® or Epoc® portable handheld blood testing device coupled with an appropriate cartridge; the modifications may include software and/or hardware modifications. The apparatus 220 comprises a detector 222, a processor 224, a memory (storage) 226 and an indicator in the form of a display screen 228. The detector 222 is adapted to receive a blood sample 230 and analyze the blood sample to generate a signal representing at least one blood chemistry parameter, and is coupled to the processor 224 to transmit the signal representing the blood chemistry parameter(s) to the processor 224. Where the apparatus 220 is a modified i-STAT® or Epoc® portable handheld blood testing device, the detector 222 may comprise an i-STAT® or Epoc® cartridge, respectively, which can receive a blood sample and then be removably inserted into the body of the apparatus 220 so as to be electrically coupled to the processor 224. In other embodiments, the detector 220 may use similar technology to analyze the blood sample. The processor 224 is adapted to compare the at least one blood chemistry parameter to a corresponding at least one resuscitatability parameter stored in the memory 226, which is coupled to the processor 224. The processor 224 and memory 226 may in some embodiments be integrated into a single unit. The display screen 228 is coupled to the processor 224 and is adapted to emit a resuscitatability indicator signal indicating potential resuscitatability in response to the processor comparing the at least one blood chemistry parameter to the corresponding at least one resuscitatability parameter. For example, the processor 224 may send a text or graphical display signal to the display 228 to display a word or symbol message which conveys the meaning "resuscitatable" or "non-resuscitatable" (or "borderline"/"indeterminate") in the case of a trinary signal). For example, a "resuscitatable" message could be in the form of text such as "This patient is resuscitatable" or "This patient is still viable", or in the form of an image, such as a caduceus (snakes winding around a winged staff) or cross, denoting medical treatment, whereas a "non-resuscitatable" message could be in the form of text such as "This patient is non-resuscitatable" or "This patient is biologically dead", or in the form of an image, such a skull, denoting death. The display screen is merely one example of an indicator. Alternatively or additionally, a speaker may be used to provide an audible signal, which may be, for example, tonal or in the form of spoken words. The indicator may also be one or more LEDs, such as a red LED to denote "non-resuscitatable" and a green LED to denote "resuscitatable", and optionally a yellow LED to denote "borderline" or "indeterminate", or a single multi-colour LED may be used as an indicator. A printer may also be used as an indicator, in which case the resuscitatability indicator signal may be printed on a substrate. Use of a printer as an indicator has the advantage of generating a non-transient written record of the resuscitatability indicator signal, and the printout may include a timestamp and/or location indicator for evidentiary purposes.

In some embodiments, the apparatus may comprise a detector coupled, for example by USB or other wired connection or Bluetooth or other wireless connection, to a suitably programmed general purpose computer, such as a smartphone, tablet computer, laptop computer or even a desktop computer of suitable size for an ambulance, such that the processor, memory and display are components of the general purpose computer.

Aspects of the present technology may be embodied within a system, a method, a computer program product or any combination thereof. The computer program product may include a computer readable storage medium or media having computer readable program instructions thereon for causing a processor to carry out aspects of the present technology. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technology may be assembler instructions, instruction-set-architecture (ISA) instructions, machine instructions, machine dependent instructions, microcode, firmware instructions, state-setting data, or either source code or object code written in any combination of one or more programming languages, including an object oriented programming language or a conventional procedural programming language. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to implement aspects of the present technology.

Aspects of the present technology have been described above with reference to flowchart illustrations and/or block diagrams of methods, apparatus (systems) and computer program products according to various embodiments. In this regard, the flowchart and block diagrams in the figures illustrate the architecture, functionality, and operation of possible implementations of systems, methods and computer program products according to various embodiments of the present technology. For instance, each block in the flowchart or block diagrams may represent a module, segment, or portion of instructions, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Some specific examples of the foregoing may have been noted above but any such noted examples are not necessarily the only such examples. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It also will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 3:
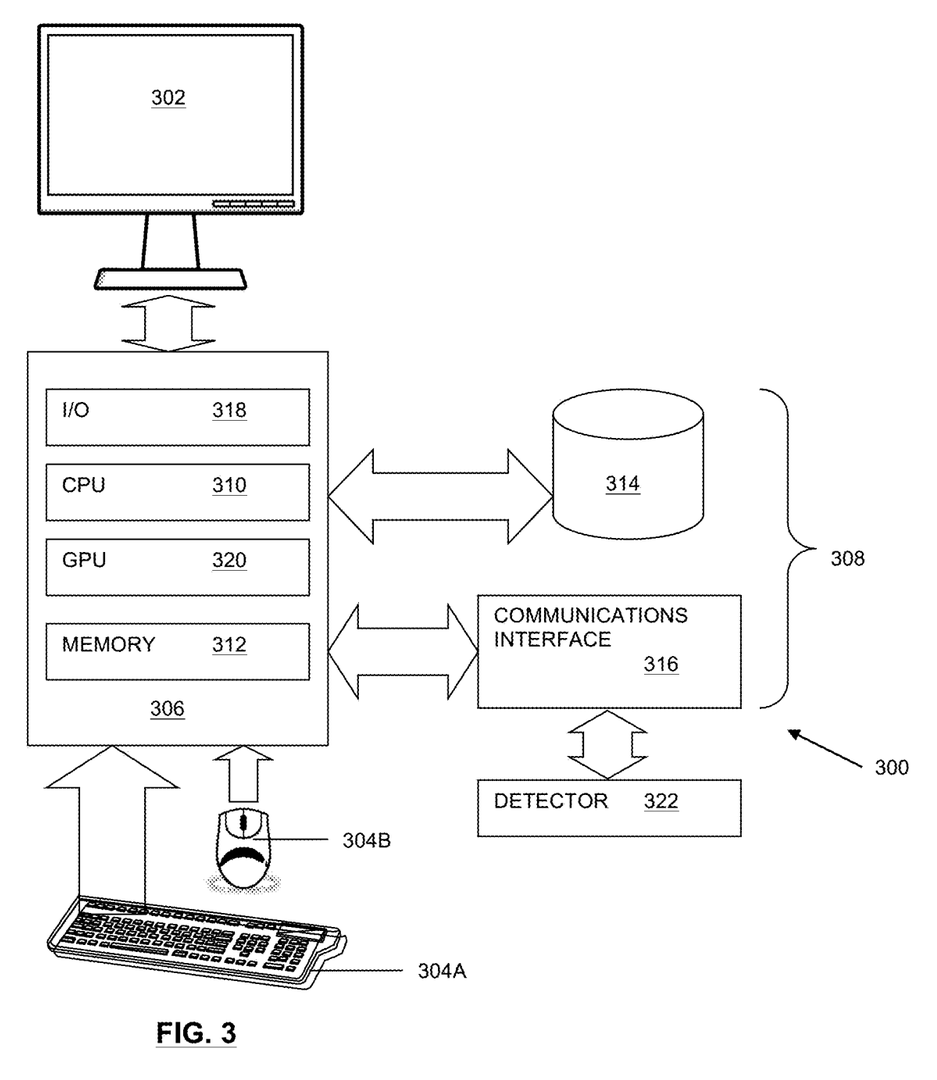
FIG. 3 is a block diagram of an illustrative computer system in respect of which the technology herein described may be implemented.

An illustrative computer system in respect of which the technology herein described may be implemented is presented as a block diagram in FIG. 3. The illustrative computer system is denoted generally by reference numeral 300 and includes a display 302, input devices in the form of keyboard 304A and pointing device 304B, computer 306 and external devices 308. While pointing device 304B is depicted as a mouse, it will be appreciated that other types of pointing device may also be used.

The computer 306 may contain one or more processors or microprocessors, such as a central processing unit (CPU) 310. The CPU 310 performs arithmetic calculations and control functions to execute software stored in an internal memory 312, preferably random access memory (RAM) and/or read only memory (ROM), and possibly additional memory 314. The additional memory 314 may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces such as those found in video game devices, removable memory chips such as EPROM or PROM, emerging storage media, such as holographic storage, or similar storage media as known in the art. This additional memory 314 may be physically internal to the computer 306, or external as shown in FIG. 3, or both.

The computer system 300 may also include other similar means for allowing computer programs or other instructions to be loaded. Such means can include, for example, a communications interface 316 which allows software and data to be transferred between the computer system 300 and external systems and networks. Examples of communications interface 316 can include a modem, a network interface such as an Ethernet card, a wireless communication interface, or a serial or parallel communications port. Software and data transferred via communications interface 316 are in the form of signals which can be electronic, acoustic, electromagnetic, optical or other signals capable of being received by communications interface 316. Multiple interfaces, of course, can be provided on a single computer system 300. A detector 322 adapted to receive and analyze a blood sample to generate a signal representing at least one blood chemistry parameter thereof is coupled to the computer system 300 via the communications interface 316.

Input and output to and from the computer 306 is administered by the input/output (I/O) interface 318. This I/O interface 318 administers control of the display 302, keyboard 304A, external devices 308 and other such components of the computer system 300. The computer 306 also includes a graphical processing unit (GPU) 320. The latter may also be used for computational purposes as an adjunct to, or instead of, the (CPU) 310, for mathematical calculations.

The various components of the computer system 300 are coupled to one another either directly or by coupling to suitable buses.

Figure 4:
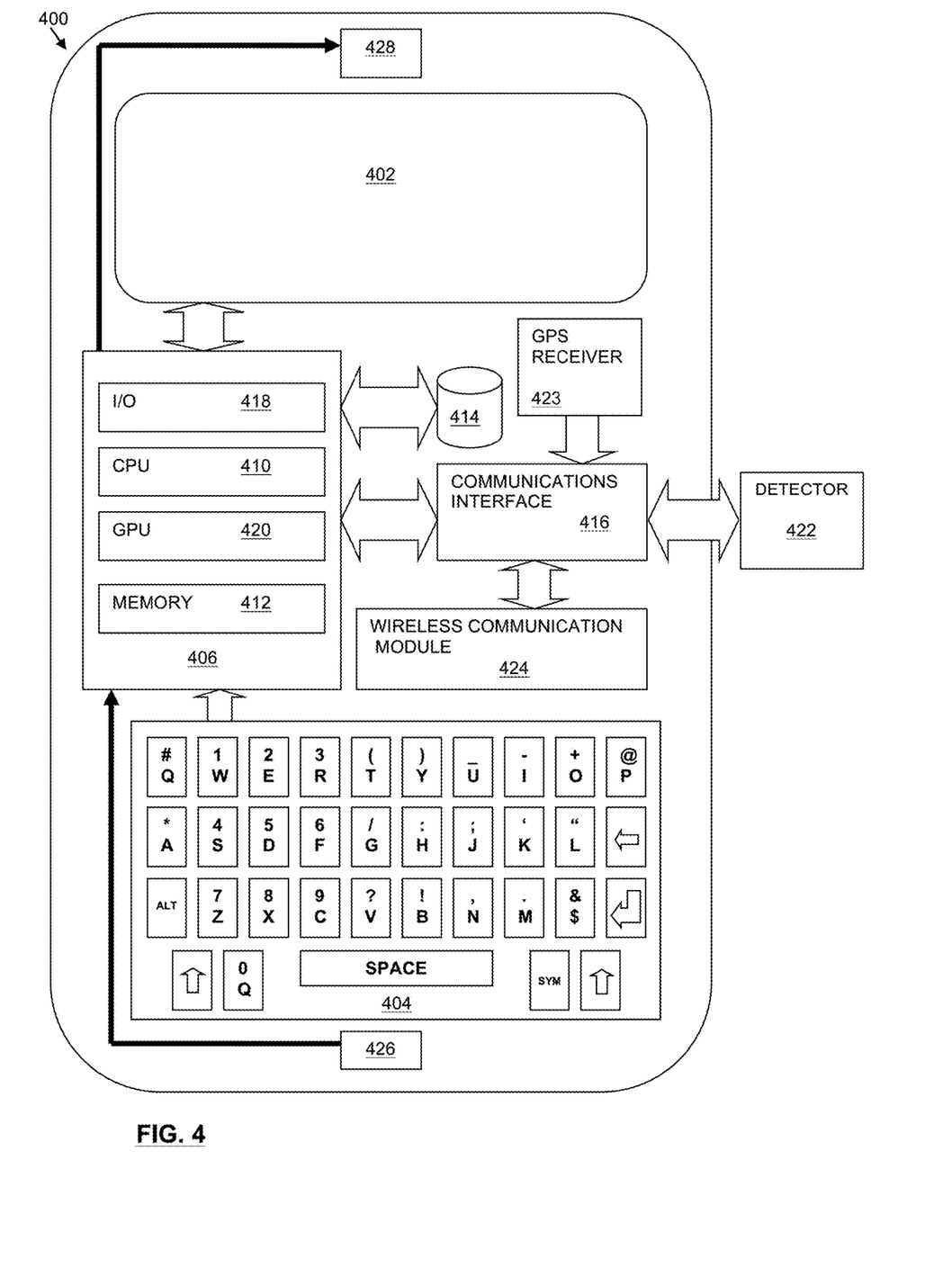
FIG. 4 is a block diagram of an illustrative smartphone in respect of which the technology herein described may be implemented.

FIG. 4 shows an exemplary networked mobile wireless telecommunication computing device in the form of a smartphone 400. The smartphone 400 includes a display 402, an input device in the form of keyboard 404 and an onboard computer system 406. The display 402 may be a touchscreen display and thereby serve as an additional input device, or as an alternative to the keyboard 404. The onboard computer system 406 comprises a central processing unit (CPU) 410 having one or more processors or microprocessors for performing arithmetic calculations and control functions to execute software stored in an internal memory 412, preferably random access memory (RAM) and/or read only memory (ROM) is coupled to additional memory 414 which will typically comprise flash memory, which may be integrated into the smartphone 400 or may comprise a removable flash card, or both. The smartphone 400 also includes a communications interface 416 which allows software and data to be transferred between the smartphone 400 and external systems and networks. The communications interface 416 is coupled to one or more wireless communication modules 424, which will typically comprise a wireless radio for connecting to one or more of a cellular network, a wireless digital network or a Wi-Fi network. The communications interface 416 will also typically enable a wired connection of the smartphone 400 to an external computer system and to other devices. A detector 422 adapted to receive and analyze a blood sample to generate a signal representing at least one blood chemistry parameter thereof is coupled to the smartphone 400 via the communications interface 416.

A microphone 426 and speaker 428 are coupled to the onboard computer system 406 to support the telephone functions managed by the onboard computer system 406, and GPS receiver hardware 423 may also be coupled to the communications interface 416 to support navigation operations by the onboard computer system 406. Input and output to and from the onboard computer system 406 is administered by the input/output (I/O) interface 418, which administers control of the display 402, keyboard 404, microphone 426 and speaker 428. The onboard computer system 406 may also include a separate graphical processing unit (GPU) 420. The various components are coupled to one another either directly or by coupling to suitable buses.

The term "computer system" and related terms, as used herein, is not limited to any particular type of computer system and encompasses servers, desktop computers, laptop computers, networked mobile wireless telecommunication computing devices such as smartphones, tablet computers, as well as other types of computer systems.

Thus, computer readable program code for implementing aspects of the technology described herein may be contained or stored in the memory 412 of the onboard computer system 406 of the smartphone 400 or the memory 312 of the computer 306, or on a computer usable or computer readable medium external to the onboard computer system 406 of the smartphone 400 or the computer 306, or on any combination thereof.

Finally, the terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited to the form disclosed. Many modifications and variations will be apparent to those of ordinary skill in the art without departing from the scope of the claims. The embodiment was chosen and described in order to best explain the principles of the technology and the practical application, and to enable others of ordinary skill in the art to understand the technology for various embodiments with various modifications as are suited to the particular use contemplated.

As can be seen from the above description, the methods described herein represent significantly more than merely using categories to organize, store and transmit information and organizing information through mathematical correlations. The methods for using blood chemistry to determine resuscitatability are in fact an improvement to the technology of on-scene life-saving and medical resuscitation, as they enable determination of whether a clinically dead patient is a candidate for resuscitation. This facilitates effective reallocation of scarce paramedic resources and avoids needless endangerment of other lives through emergency transport of a patient who is already biologically dead. Moreover, the methods for using blood chemistry to determine resuscitatability are applied by using a particular machine, namely a portable testing apparatus. As such, the methods for using blood chemistry to determine resuscitatability are confined to use by emergency first responders "in the field", as opposed to use in a hospital or other clinical setting.

Certain embodiments have been described by way of example. It will be apparent to persons skilled in the art that a number of variations and modifications can be made without departing from the scope of the claims. In construing the claims, it is to be understood that the use of a detector and processor is essential to implement the embodiments described herein.

What is claimed is:

1. An automated method for using blood chemistry to determine resuscitatability, the method comprising:
   receiving a blood sample in a detector, wherein the blood sample is liquid blood that has been withdrawn from a body;
   analyzing the blood sample by the detector to generate a signal representing at least one blood chemistry parameter of the blood sample as detected by the detector;
   transmitting the signal representing the at least one blood chemistry parameter to a processor;
   comparing, by the processor, the at least one blood chemistry parameter to a corresponding at least one resuscitatability parameter to determine whether a patient is potentially resuscitatable;
   responsive to comparing the at least one blood chemistry parameter to the corresponding at least one resuscitatability parameter, the processor causing an indicator to emit a resuscitatability indicator signal indicating potential resuscitatability;
   wherein the resuscitatability indicator signal provides a discrete indication of whether or not the patient is already biologically dead, and therefore of whether or not the patient is resuscitatable.

2. The method of claim 1, wherein the resuscitatability indicator signal is a binary signal indicating one of "resuscitatable" and "non-resuscitatable".

3. The method of claim 1, wherein the resuscitatability indicator signal is a trinary signal indicating one of "resuscitatable", "non-resuscitatable" and "borderline".

4. The method of claim 1, wherein the resuscitatability indicator signal is a visual signal.

5. The method of claim 1, wherein the resuscitatability indicator signal is an audio signal.

6. The method of claim 1, further comprising the processor recording the at least one blood chemistry parameter detected by the detector.

7. A portable testing apparatus for using blood chemistry to determine resuscitatability, the apparatus comprising:

a detector adapted to receive a blood sample wherein the blood sample is liquid blood that has been withdrawn from a body and analyze the blood sample to generate a signal representing at least one blood chemistry parameter;

the detector being coupled to a processor to transmit the signal representing the at least one blood chemistry parameter to the processor;

the processor being adapted to compare the at least one blood chemistry parameter to a corresponding at least one resuscitatability parameter stored in a memory coupled to the processor; and at least one indicator coupled to the processor, the indicator being adapted to emit a resuscitatability indicator signal indicating potential resuscitatability in response to the processor comparing the at least one blood chemistry parameter to the corresponding at least one resuscitatability parameter;

wherein the resuscitatability indicator signal provides a discrete indication of whether or not the patient is already biologically dead, and therefore of whether or not the patient is resuscitatable.

* * * * *